United States Patent [19]

Spiegelberg

[11] 4,281,650
[45] Aug. 4, 1981

[54] HERMETICALLY SEALED COMPRESS MEDICAL DRESSING

[75] Inventor: Hans Spiegelberg, Täby, Sweden

[73] Assignee: Cederroths AB, Upplands Vasby, Sweden

[21] Appl. No.: 904,500

[22] Filed: May 10, 1978

[30] Foreign Application Priority Data

Jul. 11, 1977 [SE] Sweden .............................. 7708031

[51] Int. Cl.³ .......................... A61L 15/00; A61F 7/02
[52] U.S. Cl. ..................................... 128/156; 128/268
[58] Field of Search ................ 128/155, 156, 157, 268

[56] References Cited

U.S. PATENT DOCUMENTS

| | | | |
|---|---|---|---|
| 1,262,963 | 4/1918 | McCrea | 128/268 |
| 2,296,207 | 9/1942 | Kittinger | 128/268 |
| 2,340,142 | 1/1944 | Rauner | 128/268 |
| 2,379,656 | 7/1945 | Ryberg | 128/268 |
| 2,501,544 | 3/1950 | Shroutz | 128/268 |
| 2,629,378 | 2/1953 | Barton | 128/155 |
| 2,699,779 | 1/1955 | Lustig | 128/268 |
| 2,714,382 | 8/1955 | Alcola | 128/268 |
| 2,721,550 | 10/1955 | Banff | 128/156 |
| 2,734,503 | 0/1956 | Doyle | 128/156 |
| 2,814,294 | 11/1957 | Figge | 128/156 |
| 2,836,178 | 5/1958 | Barr | 128/155 |
| 2,969,057 | 1/1961 | Simmons | 128/155 |
| 2,999,265 | 9/1961 | Duane et al. | 128/156 |
| 3,306,292 | 2/1967 | Spees | 128/268 |

Primary Examiner—Robert W. Michell
Assistant Examiner—C. W. Shedd

[57] ABSTRACT

A medical dressing is disclosed comprising an adhesive coated backing member and a medicated compress hermetically sealed between two foils adhesively secured to the backing member. In using the medical dressing the foils are separated, one foil being removed from the rest of the dressing, thus exposing the medicated compress. The compress is thus kept sterile and moist up to the moment of use.

7 Claims, 4 Drawing Figures

HERMETICALLY SEALED COMPRESS MEDICAL DRESSING

BACKGROUND OF THE INVENTION

The present invention relates to a medical dressing and more particularly to a medical dressing of the type comprising a backing member provided on one surface with an adhesive compound and a compress.

In this Specification the word compress is used in its usual sense to mean a pad or cushion which may be impregnated with a medicament or which may merely be sterile, which is adapted to be placed in contact with a wound, abrasion or the like.

It is desirable to be able to provide a medical dressing which has a compress which can be maintained in a guaranteed sterile condition until the moment of use of the dressing, or which, if impregnated with a medicament, can be kept in a moist condition until the moment of the use. It will be appreciated that whilst sterile medical dressings of this type will be of use in treating wounds or abrasions, dressings of this type may be impregnated with an anesthetic and then the dressings may be useful for effecting local anesthesia for example at the site of a proposed injection. Of course, medical dressings of this type may also be used for many other purposes. It is important that in addition to the compress being maintained in a sterile or moist condition, the dressing may be quickly and simply applied. It is also desirable that any impregnation of the compress should not come into contact with the adhesive provided on the backing member, and at the same time evaporation of liquid from the compress must be avoided. It is of course desirable that the dressing may be manufactured in a sterile condition, or may subsequently be sterilized.

OBJECTS OF THE INVENTION

It is one object of the present invention to provide a medical dressing of the type comprising a backing member provided with an adhesive layer and a compress, in which the compress is provided with means to keep the compress sterile, or if the compress is impregnated with a medicament, to keep the compress moist.

It is another object of this invention to provide a medical dressing which can readily be applied to a wound or abrasion.

It is a further object of this invention to provide a medical dressing impregnated with a local anesthetic.

BRIEF SUMMARY OF THE INVENTION

According to this invention there is provided a medical dressing comprising a backing member, an adhesive compound provided on one surface of the backing member, a compress mounted on the backing member, and means which hermetically seal the compress, the said sealing means being cuttable or tearable to expose the compress at the moment of use of the said medical dressing.

Advantageously the sealing means may comprise two foils that are superimposed and sealed together adjacent the edges to define a sealed inner space, the compress being enclosed in the inner space.

The compress may be secured to one of the foils, but in an alternative embodiment of the invention the compress may be secured to both of the foils, the compress being adapted to separate into two separate parts when the foils are separated.

The compress may be impregnated with a medicament such as a liquid, paste, or gel, and the medicament may comprise a local anesthetic.

Advantageously the foils may be sealed by being welded together to form an effective barrier for the medicament of the compress, and the foils may each comprise an aluminium foil coated with a plastics material.

In preferred embodiments of the invention the outer surface of one foil is secured, by said adhesive compound to the said backing, and advantageously a removable protective foil is provided on the areas of said adhesive not contacted by said one foil.

In one embodiment of the invention a covering flap is provided between part of the removable foil and part of the adhesive to facilitate removal of the removable foil from the adhesive, but in an alternative embodiment of the invention the removable protective foil is folded double, one part engaging the adhesive and another part protruding from the dressing to form a tab to facilitate the removal of the foil.

BRIEF DESCRIPTION OF THE DRAWINGS

In order that the invention may be more readily understood and so that further features thereof may be appreciated the invention will now be described by way of example with reference to the accompanying drawings, in which.

DETAILED DESCRIPTION OF PREFERRED EMBODIMENT OF THE INVENTION

Figure 1:
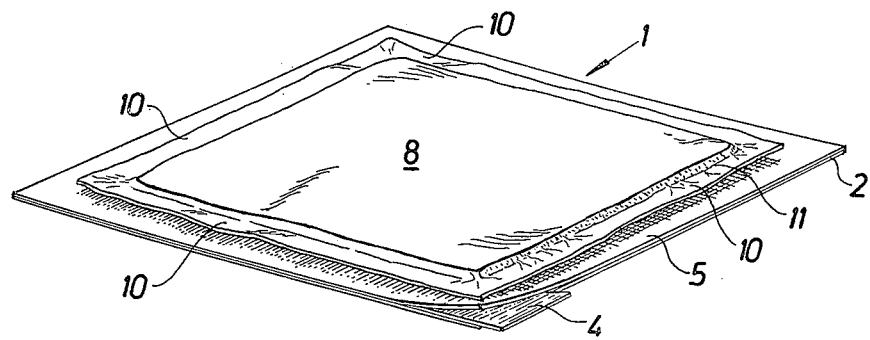
FIG. 1 is a perspective view of one embodiment of a medical dressing in accordance with the present invention.
Figure 2:
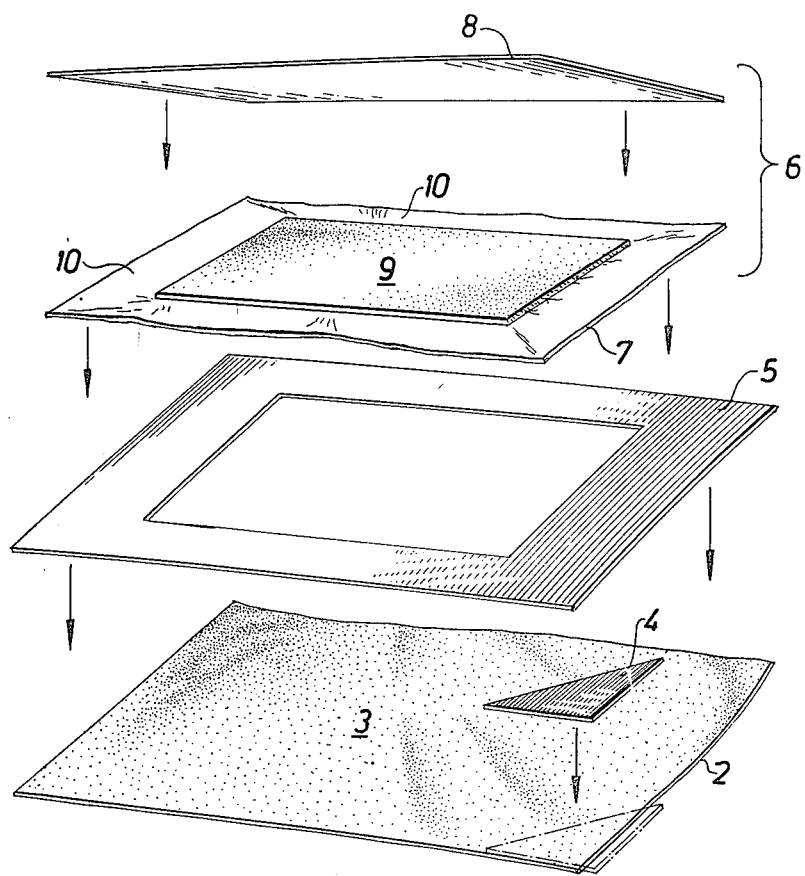
FIG. 2 is an exploded view of the medical dressing shown in FIG. 1.

Referring now to FIGS. 1 and 2 of the accompanying drawings a medical dressing 1 in accordance with the present invention comprises a rectangular backing member 2 provided on one side with a coating of a dermatologically acceptable adhesive compound 3. In one corner of the rectangular backing member 2 is a triangular covering or masking flap 4, the flap having one side in contact with the layer of adhesive compound, and a part of the flap protruding slightly beyond the edge of the rectangular backing member 2. A covering foil 5 is provided, which is a rectangular foil having a size corresponding with the size of the rectangular backing member 2, the foil 5 having a central rectangular aperture therein so that the foil 5 has the shape of a frame. The covering foil 5 is located on the backing member 2 to cover the adhesive layer 3 adjacent the edges of the rectangular backing member 2, the covering flap 4 being located between the adhesive layer 3 and the foil 5 to facilitate the tearing-off of the foil 5.

A hermetically sealed pack 6 comprising a compress 9 which is located between a lower foil 7 and an upper foil 8. The compress is preferably a compress which is impregnated with a medicament, the medicament being liquid, paste, or gel. The lower foil 7 and the upper foil 8 are made of a material which can be thermally sealed so that the two superimposed layers 7 and 8 can be sealed, together along an edge zone 10. Preferably each foil comprises a sheet of aluminum foil with a plastics material coating on one side. The sealed foils define a sealed inner space which contains the compress 9, the compress 9 thus being hermetically sealed up to the time at which the dressing is to be utilised. The compress 9 may be formed of any suitable material which may be impregnated, one particular material being that sold under the Registered Trade Mark "Savett". However, it is to be appreciated that the compress may consist of non-woven material or some other suitably absorbent material and may contain a medicament, an antiseptic agent, or a local anesthetic, and these impregnated materials may be volatile. The pack 6 is secured by means of the lower layer of foil 7 to the area of the adhesive compund 3 on the backing member 2 which is not covered by the foil 5.

When the medical dressing as illustrated in FIGS. 1 and 2 is to be utilised the pack 6 is preferably opened first by tearing or cutting off the sealed edges of the foils 7 and 8, and to facilitate this operation a suitable marking or line or mechanical weakness 11 may be provided on the edge zones 10 of the upper foil 8. The upper foil 8 can then be lifted away from the rest of the plaster, thus exposing the compress 9. The protective foil 5 may then be removed from the backing 2, with the assistance of the corner flap 4, and when the protective foil 5 has been removed from the rest of the medical dressing, the compress, with the adhesive coated backing member is ready for use and can then easily be applied to the desired area with the compress in contact with the wound or abrasion, the medical dressing being detachably secured to the skin by means of the adhesive zones previously covered by the protective foil 5.

It will be appreciated that if the dressing is to be utilized in treating a wound or abrasion the compress is maintained in a sterile condition, and preferably the compress contains an antiseptic material.

Figure 4:
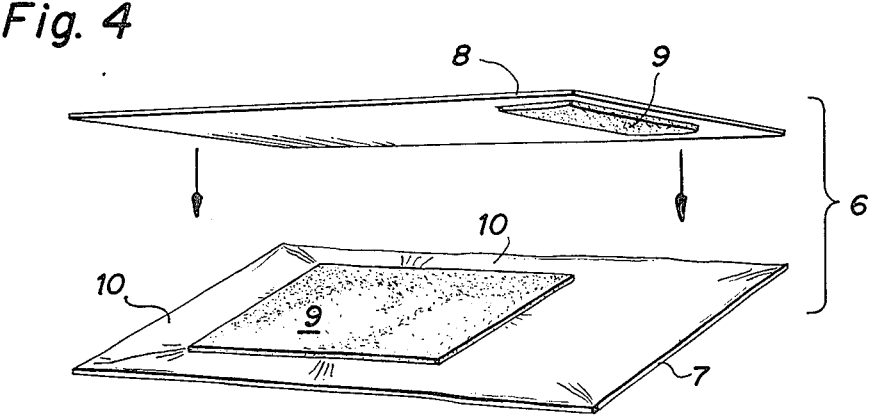
FIG. 4 is an exploded view showing a separable compress.

The invention is, of course, not limited to the specific embodiment described above, and can be varied in many ways. For example, the medical dressing need not necessarily be a rectangular shape, but may have any shape, such as, for example, circular or oval. Any suitable materials may be utilized for the upper and lower foils and for the compress and for the backing member, provided that it is always possible to provide a hermetically sealed inner space to contain the compress. Furthermore, if so desired, a part of the compress may be secured to the upper foil so that when the upper foil is pulled off this part of the compress is separated from the remaining part of the compress as seen in FIG. 4. Such a design enables the part of the compress attached to the upper foil which is pulled off to be utilized to cleanse a wound before the dressing is applied to the wound. In this particular embodiment of the invention the compress may be impregnated with a local anesthetic material, the portion of the compress which is pulled off with the upper foil being used initially to apply local anesthetic to an area which is to be injected, the rest of the dressing being applied to the injection site after the injection has been formed so that the area of the injection is further anesthetised.

It is to be appreciated that the compress may be saturated with special preparations intended for the purpose such as local anesthetics, pharmaceutical preparations, hygienic or cosmetic preparations, ointments or the like. However, a "dry" compress may also be used and can, in a dressing in accordance with the present invention, be kept sterile up to the moment of use as a result of the sealed enclosure containing the compress.

Figure 3:
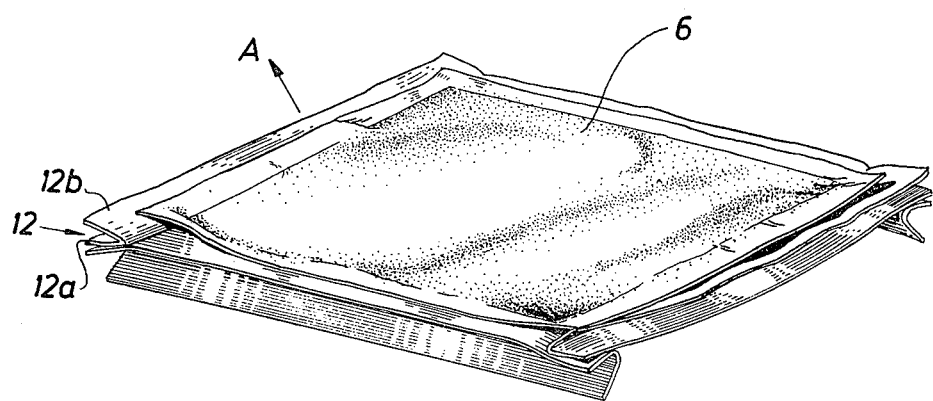
FIG. 3 is a perspective view of the second embodiment of a medical dressing in accordance with the invention.

FIG. 3 illustrates an alternative embodiment of the invention in which protective foils 12 which are folded double are used instead of the protective foil 5 described above with reference to FIGS. 1 and 2. The double folded protective foils 12 further facilitate the exposure of the adhesive edge zones of the backing member 2 when the medical dressing is to be utilized. It is to be appreciated that one part 12a of each protective foil is in contact with and covers the edge zone of the backing member 2 which is covered with the adhesive material, whereas the other part 12b of each double folded protective foil protrudes from the backing member 2 to provide a tab which can be gripped to facilitate the removal of the protective foils 12. To expose the adhesive edge zone of the backing member 2 the protective foils are removed by pulling the tab 12b in the direction of the arrow A.

The dressing shown in the accompanying drawings may be manufactured, for example, by first producing the pack 6, and subsequently applying the protective foil 5 or 12 on the side of the backing member 2 coated with the adhesive compound 3, and finally centering the pack 6 and securing the pack 6 to the backing member 2 by pressing the pack 6 against the layer of adhesive compound.

It is envisaged that medical dressings in accordance with the invention may be manufactured under sterile conditions, or may be manufactured and subsequently sterilized, for example by submitting the dressings to appropriate radiation.

I claim:

1. A medical dressing comprising in combination a backing member coated on one side with an adhesive; and a separate substantially flat package comprising a front and a rear foil hermetically sealed about their peripheral edges defining an inner space, and a compress located in said inner space and secured at least to the inner surface of the rear foil, said package being coextensive with said backing member and having the exterior surface of the rear foil adhered directly to said backing member, at least said rear foil being frangible along a line parallel at least in part to the peripheral edge of said package so as to enable simultaneous removal of a marginal strip of said rear foil and said front foil to expose the coated surface of said backing member beneath the marginal strip and the compress without removal of said compress.

2. The medical dressing according to claim 1 wherein said rear foil is frangible about the entire periphery of said package.

3. The medical dressing according to claim 1 wherein the compress located in said inner space is secured to both of the foils, and the rear foil is frangible only about a part of its periphery the compress being adapted to separate into two parts when the marginal strip is removed.

4. The medical dressing according to claim 1 wherein the foils are each an aluminium foil coated with plastics.

5. The medical dressing according to claim 1 wherein a removable protective sheet is interposed between the rear foil and the coated surface of said backing member between the peripheral edge of said package and the frangible line parallel thereto to prevent said rear foil from adhering to said backing member.

6. The medical dressing according to claim 5 including a triangularly shaped flap located in a corner of the compress package between a part of said removable sheet and said backing member.

7. The medical dressing according to claim 5 wherein said removable protective sheet is folded double, one part engaging the adhesive, and another part protruding from the dressing to form a tab to facilitate the removal.

* * * * *